(12) United States Patent
Avnir et al.

(10) Patent No.: US 9,289,402 B2
(45) Date of Patent: Mar. 22, 2016

(54) METAL ENTRAPPED BIOACTIVE COMPOSITES

(75) Inventors: David Avnir, Jerusalem (IL); Rachel Ben-Knaz, Rehovot (IL); Rami Pedahzur, Jerusalem (IL)

(73) Assignees: YISSUM RESEARCH DEVELOPMENT COMPANY OF THE HEBREW UNIVERSITY OF JERUSALEM LTD., Jerusalem (IL); HADASSAH ACADEMIC COLLEGE, Jerusalem (IL)

( * ) Notice: Subject to any disclaimer, the term of this patent is extended or adjusted under 35 U.S.C. 154(b) by 229 days.

(21) Appl. No.: 13/643,247

(22) PCT Filed: Apr. 26, 2011

(86) PCT No.: PCT/IL2011/000329
§ 371 (c)(1),
(2), (4) Date: Oct. 24, 2012

(87) PCT Pub. No.: WO2011/135563
PCT Pub. Date: Nov. 3, 2011

(65) Prior Publication Data
US 2013/0039964 A1 Feb. 14, 2013

Related U.S. Application Data

(60) Provisional application No. 61/327,957, filed on Apr. 26, 2010.

(51) Int. Cl.
*A61K 31/155* (2006.01)
*A61K 33/34* (2006.01)
*A61K 33/38* (2006.01)
*A61K 45/06* (2006.01)
*A61L 2/00* (2006.01)
(Continued)

(52) U.S. Cl.
CPC .............. *A61K 31/155* (2013.01); *A61K 33/34* (2013.01); *A61K 33/38* (2013.01); *A61K 45/06* (2013.01); *A61L 2/00* (2013.01); *B01J 31/12* (2013.01); *C02F 1/50* (2013.01); *C08K 9/10* (2013.01); *C02F 1/505* (2013.01)

(58) Field of Classification Search
None
See application file for complete search history.

(56) References Cited

U.S. PATENT DOCUMENTS

2004/0247690 A1* 12/2004 Yang .............................. 424/490
2006/0067868 A1* 3/2006 Kutsovsky .................... 423/335
(Continued)

FOREIGN PATENT DOCUMENTS

WO    WO 2010040312 A8 *  8/2010

OTHER PUBLICATIONS

Ben-Knaz et al., "Bioactive enzyme-metal composites: The entrapment of acid phosphatase within gold and silver", Biomaterials, vol. 30, Issue 7, Mar. 2009, pp. 1263-1267.*
(Continued)

*Primary Examiner* — Carlos Azpuru
*Assistant Examiner* — Casey Hagopian
(74) *Attorney, Agent, or Firm* — Browdy and Neimark, PLLC

(57) ABSTRACT

The present invention provides composites comprising at least one bioactive agent entrapped within a matrix of at least one metal; wherein said composite controllably releases at least one of said bioactive agent and metal or ion thereof, processes for the preparation of composites of the invention, compositions and products comprising composites of the invention and various uses thereof.

11 Claims, 16 Drawing Sheets

(51) Int. Cl.
*B01J 31/12* (2006.01)
*C02F 1/50* (2006.01)
*C08K 9/10* (2006.01)

(56) References Cited

U.S. PATENT DOCUMENTS

2011/0196285 A1* 8/2011 Chen et al. .................... 604/20
2012/0295790 A1* 11/2012 Yan et al. ..................... 504/273

OTHER PUBLICATIONS

Behar-Levy, et al., Chirality Induction in Bulk Gold and Silver, Adv. Mater., 2007, pp. 1207-1211, vol. 19.
Behar-Levy, et al., Entrapment of Organic Molecules within Metals: Dyes in Silver, Chem. Mater., 2002, pp. 1736-1741, vol. 14.
Behar-Levy, et al., Entrapment of Organic Molecules within Metals. 2. Polymers in Silver, Chem. Mater., 2004, pp. 3197-3202, vol. 16.
Behar-Levy, et al., Silver Doped with Acidic/Basic Polymers: Novel, Reactive Metallic Composites, Adv. Funct. Mater., 2005, pp. 1141-1146, vol. 15.
Ben-Knaz, et al., A Concept in Bactericidal Materials: The Entrapment of Chlorhexidine within Silver, Adv. Funct. Mater., 2010, pp. 2324-2329, vol. 20.
Ben-Knaz, et al., Bioactive enzyme-metal composites: The entrapment of acid phosphatase within gold and silver, Biomaterials, 2009, pp. 1263-1267, vol. 30.
Gertner, et al., Drug Delivery from Electrochemically Deposited Thin Metal Films, Electrochemical and Solid-State Letters, 2003, pp. J4-J6, vol. 6(4).

International Search Report for PCT/IL2011/000329, mail date Oct. 13, 2011.
Neouze, et al., Entrapment of an Ionic Liquid in a Metallic Silver Matrix through Precipitation, Aust. J. Chem., 2008, pp. 329-331, vol. 61.
Nesher, et al., Metal-Polymer Composites: Synthesis and Characterization of Polyaniline and Other Polymer@Silver Compositions, Chem. Matter., 2008, pp. 4425-4432, vol. 20.
Nesher, et al., Polyaniline Entrapped in Silver: Structural Properties and Electrical Conductivity, Adv. Funct. Mater., 2009, pp. 1293-1298, vol. 19.
Pachon, et al., Chiral Imprinting of Palladium with Cinchona Alkaloids, Nature Chemistry, 2009, pp. 1-6, vol. 160.
Pal, et al., Metallopharmaceuticals based on silver(I) and silver(II) polydiguanide complexes: activity against burn wound pathogens, J. Antimicrob. Chemother., 2010, pp. 2134-2140, vol. 65.
Shier, et al., Organically Doped Metals—A New Approach to Metal Catalysis: Enhanced Ag-Catalyzed Oxidation of Methanol, Adv. Funct. Mater., 2007, pp. 913-918, vol. 17.
Sinai, et al., Electrolytical Entrapment of Organic Molecules within Metals, J. Phys. Chem. B., 2009, pp. 13901-13909, vol. 113.
Yosef, et al., Entrapment of an Organometallic Complex within a Metal: A Concept for Heterogeneous Catalysis, J. Am. Chem. Soc., 2008, pp. 11880-11882, vol. 130.
Yosef, et al., Metal-Organic Composites: The Heterogeneous Organic Doping of the Coin Metals-Copper, Silver, and Gold, Chem. Mater., 2006, pp. 5890-5896, vol. 18.

* cited by examiner

METAL ENTRAPPED BIOACTIVE COMPOSITES

This invention was made with US government support under contract No. FA9550-06-1-022, awarded by the US Air Force. The Government has certain rights in this invention.

FIELD OF THE INVENTION

This invention relates to composites comprising at least one bioactive agent and at least one metal and compositions and uses thereof.

BACKGROUND OF THE INVENTION

The following publications are considered pertinent for describing the state of the art in the field of the invention:
1. Yosef, I.; Avnir, D. *Chem. Mater.* 2006, 18, 5890-5896.
2. Behar-Levy, H.; Avnir, D. *Chem. Mater.* 2002, 14, 1736-1741.
3. Behar-Levy, H.; Shter, G. E.; Grader, G. S.; Avnir, D. *Chem. Mater.* 2004, 16, 3197.
4. Behar-Levy, H.; Avnir, D. *Adv. Funct. Mater.* 2005, 15, 1141.
5. Shter, G. E.; Behar-Levy, H.; Gelman, V.; Grader, G. S.; Avnir, D. *Adv. Funct. Mater.* 2007, 17, 913-918.
6. Behar-Levy, H.; Neumann, O.; Naaman, R.; Avnir, D. *Adv. Mater.* 2007, 19, 1207.
7. Nesher, G.; Marom, G.; Avnir, D. *Chem. Mater.* 2008, 20, 4425-4432.
8. Gertner, M. E.; Schlesinger, M. Electrochem. *Solid-State Lett.* 2003, 6, J4.
9. Neouze, M. A.; Litschauer, M; *Australian Journal of Chemistry* 2008, 61(5) 329-331.
10. Yosef, I.; Abu-Reziq, R.; Avnir, D. *J. Am. Chem. Soc.* 2008 130, 11880-11882.
11. Ben-Knaz, R.; Avnir, D. *Biomaterials* 2009, 30, 1263-1267.
12. Sinai O., Avnir D. *J. Physical. Chem. B* 2009.
13. Pachn L. D., Yosef I., Markus T. Z., Naaman R., Avnir D., Rothenberg G., *Nature Chem.* 2009, 1, 160.
14. Nesher G., Aylien M., Sandaki G., Avnir D., Marom G., *Adv. Funct. Mater.* 2009, 19, 1293.

The references in this specification to any prior publication (or information derived from it), or to any matter which is known, is not, and should not be taken as an acknowledgment or admission or any form of suggestion that that prior art publication (or information derived from it) or known matter forms part of the common general knowledge in the filed of endeavor to which this specification relates.

SUMMARY OF THE INVENTION

The present invention provides a composite comprising a matrix of at least one metal, or an alloy thereof, entrapping within it at least one bioactive agent (for example. at least one therapeutically active agent, at least one biocidal agent and so forth). It is to be noted that a composite of the invention is designed to controllably release at least one of said bioactive agent and metal and/or ion thereof.

A composite of the invention broadens the activity range of the entrapped agent, reduces the probability of developing resistance to said entrapped agent, minimizes deleterious host side-effects and reduces the risk of environmental pollution while providing a controlled and/or prolonged release rate of at least one of said entrapped agent and metal (or ion thereof), keeping their concentration relatively constant in the vicinity of said composite of the invention.

Thus, in one aspect of the present invention there is provided a composite comprising at least one therapeutically active agent and at least one metal; wherein said at least one therapeutically active agent is entrapped within a matrix of said at least one metal; and wherein said composite controllably releases at least one of said therapeutically active agent and metal or ion thereof.

In a further aspect the invention provides a composite comprising at least one biocidal agent and at least one metal; wherein said at least one biocidal agent is entrapped within a matrix of said at least one metal; and wherein said composite controllably releases at least one of said biocidal agent and metal or ion thereof.

When referring to a "composite" or "composite material" (used interchangeably), it should be understood to encompass a multi-component material (fabricated from at least two compounds), comprising multiple, different phase domains, in which at least one type of phase domain is a continuous phase. Said continuous phase of a composite of the invention is, in some embodiments, said metal matrix entrapping within it said at least one bioactive agent (for example, therapeutically active agent and/or biocidal agent).

In the context of the present invention the term "bioactive agent" is meant to encompass any agent capable of exerting a beneficial biological activity, such a for example any therapeutic activity, any biocidal activity (including activity against bacteria, viruses, fungi etc. and any combination thereof), any anti-septic activity and so forth.

As used herein the term "therapeutically active agent" is meant to encompass any type of agent which may posses any medical, therapeutic or cosmetic benefits, such as for example ameliorate undesired symptoms associated with a disease or disorder, prevent the manifestation of such symptoms before they occur, slow down the progression of a disease or disorder, slow down the deterioration of symptoms associated with a disease or disorder, enhance the onset of remission period of a disease or disorder, slow down the irreversible damage caused in the progressive chronic stage of a disease or disorder, delay the onset of a progressive stage of a disease or disorder, lessen the severity or cure a disease or disorder, improve survival rate or more rapid recovery from a disease or disorder, or prevent a disease or disorder form occurring or a combination of any one of the above.

In some embodiments of the invention a therapeutically active agent may be a pro-drug or a metabolite thereof, capable of being active upon administration to a subject. In some embodiments, said agent has beneficial effects for medical use, such as for example antibacterial, antimicrobial and/or biocidal treatment of any type of surface.

In some other embodiments, when said at least one metal is Ag or Au, said at least one therapeutically active agent is other than an enzyme (such as phosphatase).

In some embodiments of the invention, at least one therapeutically active agent may be any pharmaceutical drug, medicine, medication or medicament used in the treatment, cure, prevention, or diagnosis of disease or used to otherwise enhance physical or mental well-being of a subject in need thereof, that may be used chronically or incidentally.

A non-limiting list of a therapeutically active agent utilized by the invention comprises: anti-bacterial agents, anti-viral agents, anti-fungal agents, steroidal or non-steroidal anti-inflammatory agents, biocidal agents, antiseptic agents, antibiotics, endocrinic agents, anti-proliferative agents, anti-depressants, psychiatric agents, anaesthetic agents or any combinations thereof.

In some embodiments of the invention a therapeutically active agent is a topically administered agent. In other embodiments said at least one therapeutically active agent is used in the treatment of a topical condition, disease or disorder.

The term "topically administered agent" as used herein is meant to encompass any therapeutic and/or cosmetic (cosmoceutic) agent that is capable of being administered by topical application of the agent (for example in a topical formulation of said agent), to any part of the cutaneous membrane of a subject (such as the skin or mucosal membranes (such as for example mucosal membrane of the vagina, anus, throat, teeth, gingival membrane, eyes and ears), any tissue covering a body of a subject consisting of the outer, thinner epidermis (epithelial tissue) and the inner, thicker dermis (connective tissue), that is anchored to the subcutaneous layer). It should be noted that such agents may be formulated for either systemic or local administration and may be directed for the use in the treatment of any disease or disorder, including but not limited to topical diseases, disorders or conditions.

The term "topical condition, disease or disorder" as used herein is meant to encompass any condition, disease or disorder manifested on a cutaneous body surfaces (membrane) such as the skin or mucosal membranes (such as for example mucosal membrane of the vagina, anus, throat, eyes and ears), including any tissue covering a body of a subject consisting of the outer, thinner epidermis (epithelial tissue) and the inner, thicker dermis (connective tissue), that is anchored to the subcutaneous layer. It should be noted that in some embodiments a composite or a composition of the invention is intended for topical and/or dermatological use on any type of skin area, being an exterior exposed area (such as for example areas of the skin, scalp, hair, and nails), an interior skin area such as a mucosal membrane (such as for example mucosal membrane around and on the nostrils, the lips, the ears, the genital area, the anus, the teeth, gingival membrane and so forth) or any vicinal areas in close proximity with the treated skin or mucosal membrane areas wherein said composition and agents comprised in said composition may reach via any kind of diffusion mechanisms to a skin area or mucosal membrane.

In one context of the present invention a topical condition, disease or disorder may be selected from the following non-limiting list: skin cancer (e.g. melanoma), autoimmune diseases (e.g. psoriasis), acneform eruptions (including acne, rosacea, dermatitis etc.), autoimmune, inflammatory, chronic blistering, conditions of the mucous membranes, conditions of the skin appendages, conditions of the subcutaneous fat, congenital anomalies, connective tissue diseases (including Abnormalities of dermal fibrous and elastic tissue), dermal and subcutaneous growths, dermatitis (including atopic dermatitis, contact dermatitis, eczema dermatitis, pustular dermatitis, seborrheic dermatitis etc.), disturbances of pigmentation, drug related eruptions, endocrine-related disorders, eosinophilic disease and disorders, epidermal nevi, neoplasms, cysts, erythemas, genodermatoses, infection-related disorders (including bacterium-related disorders, mycobacterium-related disorders, mycosis-related disorders, parasitic infestations, stings, and bites, virus-related diseases and disorders), lichenoid eruptions, lymphoid-related diseases and disorders, melanocytic nevi and neoplasms, monocyte- and macrophage-related disease and disorders, mucinoses, neurocutaneous, noninfectious immunodeficiency-related diseases and disorders, nutrition-related disorders, papulosquamous hyperkeratotic (including palmoplantar keratodermas), pregnancy-related disorders, pruritic, psoriasis, reactive neutrophilic diseases, recalcitrant palmoplantar eruptions, resulting from errors in metabolism, resulting from physical factors (including ionizing radiation-induced), open or subcutaneous wounds (resulting from a disease or disorder or from external impart, surgical procedure or any type of injury), aberration, urticaria and angioedema and vascular-related diseases.

In some other embodiments, said at least one therapeutically active agent is at least one antimicrobial agent and/or an anti-bacterial agent or any combination thereof. In yet other embodiments, said antimicrobial agent and/or an anti-bacterial agent are topically delivered agents. In further embodiments, said antimicrobial agent and/or an anti-bacterial agent are used for the treatment of topical diseases or disorders.

Therapeutic agents useful according to this invention include, but are not limited to biguanides, especially chlorhexidine, polymyxins, tetracyclines, aminoglycosides, rifampicin, bacitracin, neomycin, chloramphenicol, miconazole, quinolones, penicillins, nonoxynol 9, fusidic acid, cephalosporins, mupirocin, metronidazole, cecropins, protegrins, bacteriocins, defensins, nitrofurazone, mafenide, acyclovir, vancomycins, clindamycins, lincomycins, sulfonamides, norfloxacin, pefloxacin, nalidixic acid, oxolinic acid (quinolone), enoxacin, ciprofloxacin, and fusidic acid, benzyl alcohol, 2,4-dichlorobenzyl alcohol, 2-phenoxyethanol, 2-phenoxyethanol hemiformal, phenylethyl alcohol, 5-bromo-5-nitro-1,3-dioxane, formaldehyde and formaldehyde-releasing compounds, dimethyloldimethylhydantoin, glycoxal, glutaraldehyde, sorbic acid, benzoic acid, salicylic acid, p-hydroxybenzoic esters, chloroacetamide, N-methylolchloroacetamide, phenols, such as p-chloro-m-cresol and o-phenylphenol, N-methylolurea, N,N'-dimethylolurea, benzyl formal, 4,4-dimethyl-1,3-oxazolidine, 1,3,5-hexahydrotriazine derivatives, quaternary ammonium compounds, such as N-alkyl-N,N-dimethylbenzylammonium chloride and di-n-decyldimethylammonium chloride, cetylpyridinium chloride, diguanidine, polybiguanide, 1,2-dibromo-2,4-dicyanobutane, 3,5-dichloro-4-hydroxybenzaldehyde, ethylene glycol hemiformal, tetra(hydroxymethyl)phosphonium salts, dichlorophene, 2,2-dibromo-3-nitrilipropionamide, 3-iodo-2-propynyl N-butylcarbamate, methyl N-benzimidazol-2-yl-carbamate, N,N-dimethyl-2,2'-dithiodibenzamide, 2-thiocyanomethylthiobenzothiazole, C-formals, such as, 2-hydroxymethyl-2-nitro-1,3-propanediol, 2-bromo-2-nitropropane-1,3-diol, methylenebisthiocyanate, derivatives of allantoin, and combinations thereof.

In other embodiments therapeutic agents useful in accordance with the purposes of the invention include, but are not limited to bacteriocins originating from microorganisms such as for example Archaea, *E. coli* or from lactic acid-fermentation of bacteria. Non-limiting examples of bacteriocins include colicins, microcins, warnerin, warnericin, lantibiotics.

As used herein the term "biocidal agent" is meant to encompass any type of agent capable of substantially eliminating or at least slowing down the growth of harmful microorganism (such as for example bacteria), virus, fungi or any combination thereof. In some non-limiting embodiments, a biocidal agent is selected from: a non-oxidizing biocides (for example compounds used in industrial water treatment such as quaternary ammonium compounds, thiazolines, isothiazolinones, antimicrobial agents, anti-fungal agents, anti-viral agents, antibacterial agents), biocidal alloys (metallic silver-copper alloys, silver-zinc alloys), oxidizing biocides (halogen-sources and peroxy-compounds).

In some embodiments of the present invention an antimicrobial agent is selected from chlorohexidine.

In some embodiments of the invention at least one metal is selected from: Au, Ag, Cu, Zn, Pt, Pd, Ti, Co, or any combination thereof. In other embodiments said at least one metal is in a metallic state. In yet further embodiments said at least one metal is radioactive metal, or a combination thereof with non-radioactive metal. In further embodiments at least one metal is selected from: Ag, Cu and any combinations thereof. In yet further embodiments, at least one metal in a composite of the invention is Ag. In yet further embodiments, at least one metal in a composite of the invention is Cu.

It should be understood that when referring to two or more metals comprised in the composite of the invention forming a metal matrix, said metal matrix may be composed of a mixture of at least two metals or a metallic alloy, such as for example alloys of Ag and Zn, alloys of Ag and Au, alloys of Ag and Cu, alloys of Cu and Zn and so forth. An alloy according to the invention is a partial or complete blend of one or more elements in a metallic matrix. A complete solid solution alloys displays single solid phase microstructure, while a partial solution may have two or more phases that may be homogeneous and/or heterogeneous in distribution.

When referring to a matrix formed by said at least one metal, it should be understood to encompass a three dimensional continuous aggregate of metallic crystallites and/or particles (in some embodiments particles have at least one dimension having a length of between about 5 nm to about 100 nm) connected via physical and/or chemical bonds such as for example electrostatic and/or Van-der-Waals forces, thereby forming pores and inner voids in said three dimensional aggregate capable of entrapping molecule(s) therein.

In some embodiments, said metal matrix entrapping said agent(s) has pore size (and/or inner voids formed by three dimensional matrix structure) of between about 0.1 to about 30 nm. In some other embodiments, the pore size of a metallic matrix of the invention may be chosen so as to provide the prolonged and/or controlled release of the entrapped at least one agent within it. Thus, the pose size of a metallic matrix of the invention may depend, but is not limited to, at least one of the following features: molecular weight and size of the entrapped agent, the desired release profile of the agent and/or metal (or ion thereof), formulation of the product comprising at least one composite of the invention, the end use of a composite of the invention and so forth.

In this context it should be noted that said metallic component of a composite of the invention may serve either as a carrier of the entrapped agent(s), and/or may posses any independent activity which may result in a beneficial effect (such as for example a therapeutic effect, a biocidal effect and so forth) that is similar or different than the effect of the entrapped agent(s), thereby providing a broadened activity effect that may be an additive effect and/or a synergistic effect to the effect of the entrapped agent of the composite of the invention.

In some embodiments, a metal having beneficial effect (e.g. having biocidal properties) is metallic silver or metallic copper or any other known bioactive metals.

Without being bound by theory, the biocidal activity of metallic silver or copper is associated with its potency at very low concentrations. For example, under certain conditions bulk silver releases trace amounts of silver cations ($Ag^+$) from its surface, which are strongly toxic to a wide range of microorganisms including gram negative and gram positive bacteria, fungi and even viruses. The proposed mechanism for metallic silver's biocidal activity is closely related to the strong interactions of silver ions with thiol groups in enzymes and in other vital proteins which lead to their inactivation. Thus, exposure to silver ions damages multiple components of bacterial cell metabolism, including the permeability of the cell membrane which leads to gross cellular structural changes, blockage of transport processes and interference in the activity of vital enzymatic systems such as the respiratory cytochromes, alteration of proteins and binding to DNA and RNA which affect their functionality.

When relating to said at least one agent (for example therapeutic agent, antibacterial agent, bioactive agent, biocidal agent) being entrapped within said matrix, it should be understood to encompass the enclosure of at least one type of agent in the inner voids and/or pores formed in said metallic matrix. The agents are held enclosed within the metallic matrix via multiple physical and chemical adsorptive interactions such as covalent, electrostatic and Van-der-Waals, $\pi$-$\pi$ and/or $\sigma$-$\pi$ interactions, charge-transfer interactions and hydrophobic interactions.

An entrapping (or doping) process of a metal or metal alloy employed by the invention includes, but is not limited to, a room temperature metal synthesis by chemical reduction of the metal-cation, in either aqueous or organic phases, with either homogenous (solvent-soluble) or heterogeneous (solvent-insoluble) reducing agent, carried out in the presence of the desired organic molecule. The entrapped active molecule(s) remain chemically intact (and thus retains their activity), and reside mainly within the pores formed during the growth and aggregation of the metal crystallites. The metallic matrix is suitable to serve as a carrier for the active agent(s), making them accessible for chemical interaction with external reagents (for example by diffusion of such external reagents into the porous material or by timed (prolonged and/or sustained) controlled release of the active entrapped agents to the close environment).

In some embodiments of the invention, the weight ratio between entrapped at least one agent (bioactive, therapeutic and/or biocidal agent) and at least one metal is from about 0.05 to about 20 of the total composite. The proper ratio of entrapped agent and at least one metal is chosen so as to provide the sought effect of a composite of the invention.

In some embodiments a composite of the invention may be in the form of granules, particulate matter, powders, colloidal solution or emulsion, soaked within a filler, discs, thin films, flakes, fibers etc. The size and shape of said composite material of the invention is dependant on the type of metal used, type of therapeutic agent(s) entrapped and their respective concentrations as well as the desired release rate of at least one of said entrapped agent and/or metal or metal ion from the composite.

At least one of said agent (bioactive agent, therapeutic agent and/or biocidal agent) entrapped within a metallic matrix of a composite of the invention and/or said metal or ion thereof are capable of being released to the vicinal environment of said composite in a controlled manner. Said controlled release profile may be predetermined by changing the parameters of the aggregated composites, such as the elementary grain size, compactization under pressure, external coatings, impregnation of composite in suitable carriers (such as for example filters, gels, etc.), matrix pore size, weight ratios of the composite components (at least one metal and at least one active agent). Such parameters influence the rate of release of at least one of agent and of metal (or ion thereof), and hence the dosing regimen and also the hydraulic characteristics of the composite materials which determine their suitability for flow-through applications. In some embodiments, said release of at least one entrapped agent from a composite of the invention is in a rate of about half-content of said at least one agent per hour to about half-content of said at least one agent per month. In some embodiments a composite of the invention controllably release at least one agent entrapped within its metallic matrix. In other embodiments, a composite of the invention controllably releases at least one agent and at least one metal (or ion thereof, which may be a cation of said metal, and anion of said metal or any combination thereof). The release rate of said entrapped at least one agent and the release of a metal (or ion thereof) may be either independent of one another or dependant on one another.

In another aspect the invention provides a composite comprising at least one biocidal agent entrapped within a matrix of at least one metal, for use in disinfection of liquids.

As used herein the term "disinfection of liquids" is meant to encompass remove (inactivate or kill) at least a part of harmful microorganisms (for example bacteria), viruses, fungi etc. from a treated liquid to the extent that said liquid may be considered safe for various uses (such as for example when the liquid treated is waste water resulting from industrial waste, disinfection of waste water may be utilized for non-potable applications (industrial and recreational) and/or potable water applications).

In some embodiments of the invention a liquid suitable for disinfection includes waste water. It is to be understood that such waste water may originate from any type of industrial process, previous domestic, agricultural and other uses and so forth. Non-limiting examples of waste water sources include: recreation water facilities, swimming pools and spas, cooling systems, water-intensive industries such as the paper industry, wastewater and effluents, air conditioning systems, hot and cold closed water systems, aquaculture such as fishponds, soil-less (hydroponic) agriculture, greenhouses, etc.

In some embodiments a composite of the invention (or a composition or product comprising it) may be used in the continuous disinfection of closed-loop recirculation water systems (such as for example cooling systems). Thus, under some embodiments, a composite of the invention enables the disinfection of any type of bio-fouling agents, sessile (biofilm), planktonic microorganisms accumulated in the closed-loop water system, providing long-term residual effectiveness.

In further embodiments, a composite of the invention can be utilized in the disinfection of hot-water systems, wherein multidrug resistance microorganisms proliferate (such as for example *Legionella pneumophila*).

In some other embodiments of the invention a liquid suitable for disinfection includes large scale water sources, either from a natural source (such as surface water or groundwater) or desalinated water (for example from reverse osmosis systems).

In a further aspect the invention provides a composite comprising at least one therapeutically active agent and/or bioactive agent entrapped within at least one metal, for use in therapy (i.e. in the treatment, evaluation or diagnosis of a disease, disorder or condition).

In another one of its aspects, the invention provides a composition comprising at least one composite according to the invention. In some embodiments, said composition is a therapeutic composition.

As used herein "therapeutic composition" means therapeutically effective amounts of a composite of the present invention, together with suitable diluents, preservatives, solubilizers, emulsifiers, adjuvant and/or carriers. Such compositions may be liquids or lyophilized or otherwise dried formulations and include diluents of various buffer content (e.g.; Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Suitable routes of administration for compositions of the subject invention are oral, buccal, sublingual, via feeding tube, topical, dermal, transdermal, or parenteral (including subcutaneous, intramuscular, intravenous and intradermal) administration. Under specific embodiment, a composite of the invention and/or a composition comprising it is formulated for topical administration.

The exact dose and regimen of administration of a composition of the invention will necessarily be dependent upon the therapeutic effect to be achieved and may vary with the particular formula, the route of administration, and the age and condition of the individual subject to whom the composition is to be administered.

The present invention thus also provides pharmaceutical compositions of the invention in admixture with pharmaceutically acceptable auxiliaries, and optionally other therapeutic agents. The auxiliaries must be "acceptable" in the sense of being compatible with the other ingredients of the composition and not deleterious to the recipients thereof.

In some embodiments, a pharmaceutical composition of the invention further comprises at least one pharmaceutically active agent.

A composition of the invention may be prepared by any method well known in the art of pharmacy. Such methods include the step of bringing in association the ingredients with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents.

Therapeutic compositions suitable for oral administration may be presented as discrete dosage units such as pills, tablets, dragées or capsules, or as a powder or granules, or as a solution or suspension. For parenteral administration, suitable compositions include aqueous and non-aqueous sterile injection. A composition of the invention may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated.

In some embodiments, a composition of the invention is formulated for topical administration. Topical formulations include but are not limited to an ointment, a cream, a lotion, oil, an emulsion, a gel, a paste, milk, an aerosol, a powder, foam, a wash, a transdermal patch, a topically applied bandage, membrane, films, patch or an externally placed device and any combination thereof.

A topical formulation according to the invention may also comprise a dermatologically, cosmetic or pharmaceutically acceptable carrier, diluent or excipients in which composites of the invention may be e.g., dispersed or suspended. The composite of the invention may be easily dispersed or suspended in such a carrier, diluent or excipients, by for example mixing to achieve an effective dispersion or suspension. If necessary, high shear forces may be applied to facilitate fast and efficient mixing of the composites of the invention in the carrier.

The term "treatment of a disease, disorder or condition" as used herein refers to the administering of a therapeutic amount of a composition of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

In some embodiments of the invention a composite of the invention and/or a composition comprising it, may be used in the treatment of a topical disease, disorder or condition. Treatment may further include improving appearance of a topical surface of a subject, encompassing any visible improvement of the condition of a skin area or mucosal membrane treated by a composition or a kit of the invention. The improvement may appear as any change in the skin or mucosal membrane color, smoothness, uniformity, degree, intensity and number of lesions or wounds on the subject's skin or membrane area which may be due to any kind of skin condition or disorder such as in some embodiments bacterial, viral or fungal infection etc.

The "effective amount" for purposes disclosed herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

In some embodiments of the invention a composite of the invention comprises metallic silver. In further embodiments of the invention a composite of the invention comprises metallic copper. In other embodiments, a composite of the invention comprises metallic silver and a biocidal agent. In yet further embodiments, a composite of the invention comprises metallic copper and a biocidal agent. In further embodiments said biocidal agent is Chlorehxidine digluconate.

Chlorehxidine digluconate (CHD) is a widely used, broad-spectrum antiseptic agent capable of damaging the membranes of both gram positive and negative bacteria, and its entrapment within silver was carried out by using the homogenous methodology, namely sodium hypophosphite as a reducing agent for silver cation; the resulting CHD@Ag composite was tested for its bactericidal action against wild type E. coli which was only slightly affected by silver or CHD at the same concentrations and conditions.

Without being bound by theory it is assumed that the mechanism of action of active agents entrapped in metal, such as the CHD@Ag or CHD@Cu composites is due to the ability of CHD to disrupt bacterial membranes making them more penetrable to the $Ag^+$ or $Cu^{+2}$ ions which may enter the cell and bind to intracellular moieties such as the DNA and inhibit its replication processes, or translation or any biological activity related or dependent on DNA metabolism. The different mechanisms of action of Ag/Cu and of CHD are the source of combined synergetic activity. For the entrapment of an organic biocidal agent within a biocidal metal, the gradual co-release of both CHD and ionic Ag/Cu from the metallic matrix is an important feature. As the CHD molecules gradually leave their hosting metallic pores, the extent of the exposed metallic surface increases and thus, the release of $Ag^+$ (or $Cu^{+2}$) increases, and the extended time-release of the composite enables one to achieve an extended biocidal effectiveness.

In another one of its aspects, the invention provides a use of a composite comprising at least one therapeutically active agent and at least one metal, wherein said at least one therapeutically active agent is entrapped within a matrix formed by said at least one metal, and wherein said composite controllably releases at least one of said therapeutically active agent and metal or ion thereof, for the preparation of a therapeutic composition.

In a further aspect, the invention provides a use of a composite comprising at least one therapeutically active agent and at least one metal, wherein said at least one therapeutically active agent is entrapped within a matrix formed by said at least one metal, and wherein said composite controllably releases at least one of said therapeutically active agent and metal or ion thereof, for the preparation of a topically active composition.

In yet another aspect, the invention provides a use of a composite comprising at least one therapeutically active agent and at least one metal, wherein said at least one therapeutically active agent is entrapped within a matrix formed by said at least one metal, and wherein said composite controllably releases at least one of said therapeutically active agent and metal or ion thereof, for the preparation of a surface treating composition.

When referring to a surface treating composition it should be understood to encompass a composition capable of disinfecting against and/or preventing the proliferation of any type of cell, microorganism or bacteria on said surface.

In another aspect, the invention provides a use of a composite comprising at least one therapeutically active agent and at least one metal, wherein said at least one therapeutically active agent is entrapped within a matrix formed by at least one metal, wherein said composite controllably releases at least one of said therapeutically active agent and metal or ion thereof, for the preparation of a pharmaceutical composition for the treatment of a disease or disorder selected from: topical diseases or disorders, viral or bacterial inflammation, proliferative disease or disorders, psychiatric disease or disorders, proliferative diseases or disorders, endocrine disease (such as for example Type 1 or Type 2 diabetes) or disorder, infectious diseases, gastrointestinal diseases (such as for example ulcer hemorrhages, gastrointestinal diabetes) or any combination thereof.

In another one of its aspects the invention provides a use of a composite comprising at least one biocidal agent and at least one metal, wherein said at least one biocidal agent is entrapped within a matrix of said at least one metal, and wherein said composite controllably releases at least one of said biocidal agent and metal or ion thereof, for the preparation of a liquid-disinfection composition.

In some embodiments a liquid-disinfection composition may further comprise at least one active agent (such as for example a disinfecting agent, a further biocidal agent, a water-treatment agent, a nutrient, a vitamin). Said liquid-disinfecting composition may also comprise additional non-active agents suitable for formulating said composition for its end use. Such additives may include, but are not limited to: diluents, adjuvants, compacting agents, dispersing agents, emulsifying agents, granulating agents, microencapsulating agents and so forth.

In a further aspect the invention provides a method of treating a disease or disorder comprising administrating to a subject in need thereof at least one composite comprising at least one therapeutically active agent and at least one metal, wherein said at least one therapeutically active agent is entrapped within a matrix formed by at least one metal, and wherein said composite controllably releases at least one of said therapeutically active agent and metal or ion thereof.

In some embodiments, said disease or disorder is selected from topical diseases or disorders, viral or bacterial inflammation, proliferative disease or disorders, psychiatric disease or disorders, proliferative diseases or disorders, endocrine disease (such as for example Type 1 or Type 2 diabetes) or disorder, infectious diseases, gastrointestinal diseases (such as for example ulcer hemorrhages, gastrointestinal diabetes) or any combination thereof.

In another one of its aspects the invention provides a method of disinfecting a liquid comprising contacting said liquid with an effective amount of at least one composite comprising at least one biocidal and/or bioactive agent and at least one metal, wherein said at least one agent is entrapped within a matrix of said at least one metal, and wherein said composite controllably releases at least one of said agent and metal or ion thereof.

In a further aspect, the invention provides a product (and/or a device) comprising at least one composite comprising at least one agent (bioactive, therapeutically active or biocidal agent) and at least one metal, wherein said at least one therapeutically active agent is entrapped within a matrix of said at least one metal.

Another product provided in the present invention comprises at least one composite comprising at least one biocidal agent and at least one metal, wherein said at least one biocidal agent is entrapped within a matrix of said at least one metal, and wherein said composite controllably releases at least one of said agent and metal or ion thereof.

The present invention envisages a product comprising at least one composite of the invention for use in disinfection of liquids (such as for example: water, waste water (industrial or other), closed-loop circulating water systems, natural water sources, desalinated water sources, etc.).

Such products of the invention may include also additional elements useful for treating liquids, for example, electro-chemically generated chlorine (from sodium chloride) and ionization systems for the simultaneous release of silver and copper ions from special electrodes.

Additional uses of a product for disinfection of liquids envisaged by the invention are Point of Use (POU) systems which are used locally to self-treat liquids (e.g. water) at the use level. Such point of use systems may be stationary-attached to faucets of the water distribution systems, or can be self sustained-mobile (hand held or larger) manually operated by the consumer to obtain and treat water from available sources. Examples of such systems are; Personal Water Bottle (consists of a bottle and a filter), Pour Through (gravity as the driving force causes water to drip through a pitcher), Faucet Mount (mounted on an existing kitchen sink faucet), Counter-Top Manual Fill (placed on a counter and filled by pouring water into the system and activating it for a batch of water), Counter-Top connected to sink faucet (placed on a counter and connected by tubing to an existing kitchen sink faucet).

A disinfecting product of the invention may also be used in industrial systems, such as for example in in-line disinfection of re-circulating water system. In some embodiments, such a product of the invention may be used in installation of flow-through elements which are fitted into the piping system. Another example is the use of a disinfection product of the invention in injection of a liquid formulation of the product into the piping via injectors (using positive or negative pressure) or to holding tanks that are part of the recirculation system.

A product or a device as used herein may include any type of medical device used for medical purposes in patients, in diagnosis, therapy or surgery. If applied to the body of a subject, the effect of the medical device is primarily physical, in contrast to pharmaceutical drugs, which exert a biochemical effect. A device or product may be selected from the following non-limiting list: anesthesia units, anesthesia ventilators, apnea monitors, argon enhanced coagulation units, aspirators, auto transfusion units, electrosurgical units, invasive blood pressure units, pulse oximeters, urological and/or vascular stents, endoscopes, surgical drill and saws, laparoscopic insufflators, phonocardiographs. Other products falling within the scope of the invention include also devices for disinfecting liquids, such as for example water.

Additionally, a composite of the invention (or a composition or product comprising at least one composite of the invention) may be impregnated in a transdermal patch or skin patch which may be placed on a skin of a subject to deliver a specific dose of an entrapped agent, for the promotion of healing to a disease or disorder. Such transdermal patches may include also plasters, bandages and pads impregnated with at least one composite of the invention.

In a further aspect, the invention envisages a process for producing a composite comprising at least one agent (bioactive agent, therapeutic agent and/or biocidal agent) and at least one metal; wherein said at least one agent is entrapped within a matrix of said at least one metal; said process comprising: providing a mixture of at least one metal salt with at least one agent; subjecting said mixture to conditions enabling the reduction of said at least one metal salt; thereby forming a matrix of said at least one metal entrapping said at least one agent.

In the context of the invention, it is noted that the choice of said at least one metal reducing agent is made in view of the characteristics and properties of the metal salt and the metal matrix to be achieved. In some embodiments said metal salts may be selected from chlorides, bromides, nitrates, acetates, sulphates, phosphates, perchlorates, hydroxides, cyanides, alkanoates, (substituted) benzoates, (substituted) phenolates salts of said at least one metal or any combinations thereof. The corresponding at least one reducing agent employed may be selected from the following non-limiting list phosphites, phosphins, sulphites, thiosulphates, metal hydrides, borohydrides, $LiAlH_4$, low-oxidation state cations (e.g., ferrous cation), hydrazine, silanes, hydrogen, reducing metal or metal alloys (having a comparatively more negative reducing potentials, such as Zn and Al), organic acids such as oxalic acid and formic acid, and any combinations thereof.

In some embodiments of a process of the invention said conditions enabling the reduction of said at least one metal salt comprise adding to said mixture at least one metal reducing agent.

In other embodiments, said mixture of at least one metal salt with at least one agent further comprises at least one solvent.

In further embodiments said at least one solvent is at least one aqueous or at least one organic solvent or any mixture thereof. In yet further embodiments, said at least one metal reducing agent is substantially dissolved in said at least one solvent. In other embodiments, said least one metal reducing agent is substantially insoluble in said at least one solvent.

In another embodiment, a process of the invention further comprises compacting or pressing said formed composite.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any integer or step or group of integers and steps.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
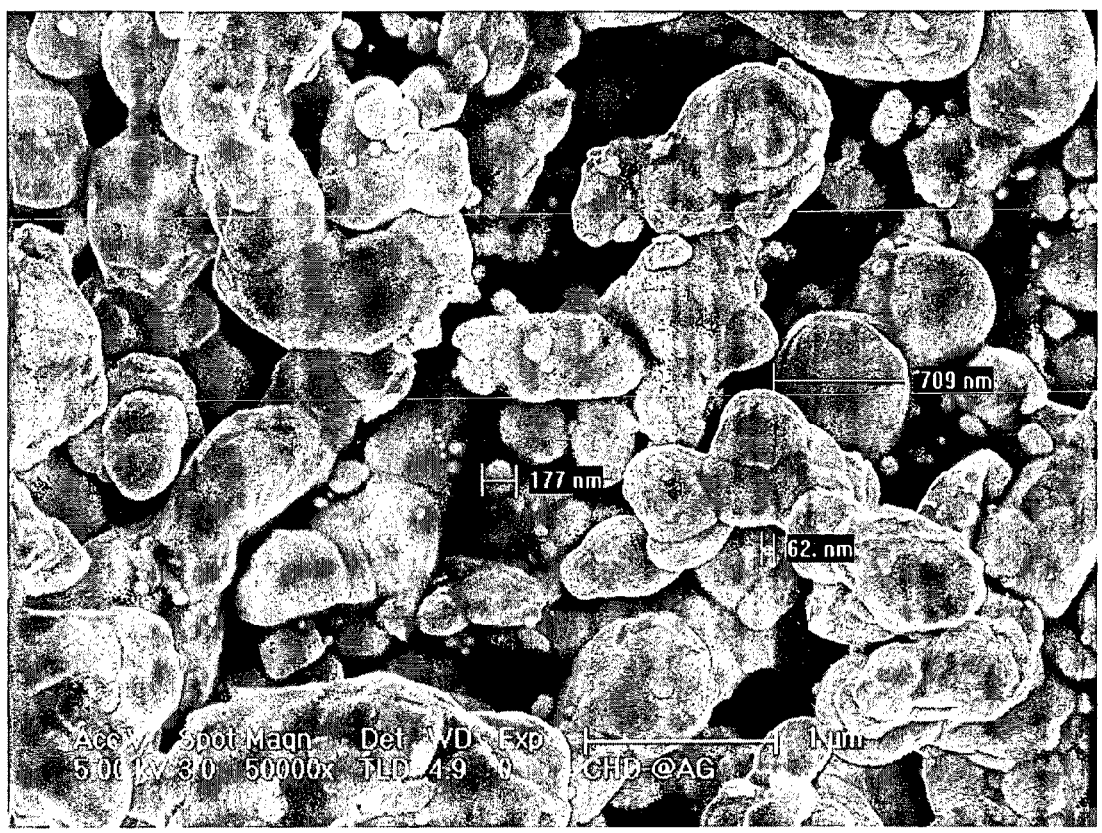
FIGS. 1A-1B show a high-resolution SEM image of silver, within which chlorohexidine is entrapped (CHD@Ag) (FIG. 1A). EDAX analysis of CHD@Ag (FIG. 1B).

Materials $AgNO_3$ (Metalor), $CuSO_4$ (Aldrich), $NaH_2PO_2 \cdot xH_2O$ (Aldrich, based on data provided from the producer, x in the phosphite is approximately 0.2). Chlorhexidine digluconate (CHD) solution, 20% in water, $Na_2HPO_4$, $KH_2PO_4$, NaCl, KCl (Sigma). Nutrient Agar (DIFCO). Sodium thioglycolate, sodium thiosulfate, lecithin, and HEPES (Acros Organics). Tween 80 (polyethylene glycol sorbitan monooleate) (Fluka)

Entrapment Procedure

The Entrapment of CHD within Silver:

3.03 g (0.018 mol) of $AgNO_3$ was dissolved in 100 ml of distilled water. 0.76 ml of 0.236 M CHD solution (0.18 mmol) was added and the combined solution stirred for 2 h at 30° C. Then 1.18 g of $NaH_2PO_2 \cdot xH_2O$ was added and the combined slurry was stirred at 30° C. for 4 days. The resulting precipitate was filtered, washed with three portions of 100 ml of distilled water and dried overnight under vacuum. The resulting composite, 1.9 g of CHD@Ag contained 0.19% mol CHD/mol silver, which is 20% of the biocide initial amount.

The Entrapment of CHD within Copper:

1.25 g (7.8 mmol) of $CuSO_4$ were dissolved in 25 ml of distilled water. 0.465 ml of 0.218 M CHD solution (0.10 mmol), 1.385 g of $NaH_2PO_2 \cdot xH_2O$ (0.016 mol) were added and the combined slurry was stirred at 55° C. for 7 h under Argon. The resulting precipitate was filtered, washed with three portions of 25 ml of distilled water and dried overnight under vacuum. The resulting composite, 0.47 g of CHD@Cu contained 0.16% mol CHD/mol copper, which are 13% of the biocide initial amount.

Testing for Possible Adsorption of CHD on Silver

For comparing adsorption to entrapment, metallic silver was prepared as described above but in the absence of CHD. The resulting powder was stirred for 4 days in a solution of CHD under the conditions and the concentrations of the entrapment experiment. The resulting solid was analyzed by TGA and did not exhibit any weight loss which can be contributed to CHD.

Extraction and CHD Release Profile Experiments

Extraction in MeOH:

0.1 g of CHD@Ag or CHD@Cu composite was suspended and stirred in 100 ml of MeOH for 24 h. Then the powder was filtered and dried under vacuum overnight. Stability of CHD to the entrapment procedure was tested by measuring the spectra of the extract of CHD@Ag in comparison to the spectra of CHD dissolved in MeOH.

CHD Release Profile from CHD@Ag Powder:

leaching of CHD into HEPES buffer which was used as the experimental medium for the antibacterial test was measured by stirring 0.1 g of CHD@Ag composite powder in HEPES buffer (0.04 M, pH 7.4) and following spectroscopically the release of CHD through its maximum absorption at 255 nm. The scattering of the composite powder was eliminated by subtraction of the absorption at 320 nm from the measured values. Readings were taken every minute for the first 10 min, every 2 min for the successive hr and then every 5 min for a total of 2.5 hr.

CHD Release Profile Form CHD@Ag-Disc:

CHD@Ag powder was pressed by applying a pressure of 9 ton over 0.2 g of the composite powder. The disc was sliced into pieces of 3.0 mg. Then, the 3.0 mg sliced composite disc was stirred with 3 ml of HEPES buffer (0.04 M, pH 7.4) in a quartz cuvette. Leaching of CHD was followed spectroscopically similarly as mentioned above, once a day for a total of 7 days.

CHD Release Profile from CHD@Cu Powder:

3.0 mg of CHD@Cu composite powder was stirred with 3 ml HEPES buffer in a quartz cuvette and the leaching of CHD was followed spectroscopically similarly as mentioned above. Readings were taken every minute for the first 3 hours, after 24 hours and after 31 hours.

Bactericidal Kinetic Tests

A wild-type *Escherichia coli* strain MG1655 was used as a target organism to evaluate the bactericidal efficacy of the active ingredients i.e. CHD, metallic and ionic Ag and the CHD@Ag composite. Bacteria were maintained on MacConkey agar plates at 40 C. Prior to each experiment, an overnight culture was prepared by seeding single colonies into 30 ml of Luria Bertani (LB) broth at 37° C. with shaking. This overnight culture was then washed three times by centrifugation (10 min, 4850 rpm, at 25° C.) and resuspended in HEPES buffer (0.04M, pH 7.4). The resulting washed pellet was resuspended in HEPES and brought to an optical density (OD590) of 0.3 which corresponds to ca. 108 CFU/ml. Enumeration of bacteria was performed by serial dilution and plating via the pour-plate technique. The inoculated plates were incubated at 37° C. for 24 h and bacterial concentrations were determined by enumerating the resulting CFUs.

The bactericidal kinetic tests were carried out in five acid-washed 500 ml Erlenmeyer flasks filled with 200 ml HEPES buffer. The flasks were capped with dense paper caps to allow oxygen supply. Typically, the active ingredients at the desired concentrations and combinations were added first and then 2.0 ml of the *E. coli* suspension was added to final concentration of ca. 106 CFU/ml. The active ingredients included one of the following: CHD@Ag composite, MeOH-extracted composite, AgNO$_3$ solution, CHD solution and combinations thereof in final concentrations and the amounts which are summarized in Table 1.

TABLE 1

| Compositions | Final concentration [ppm] |
|---|---|
| CHD@Ag composite | 50.0 |
| MeOH-extracted composite | |
| AgNO$_3$ solution (1.2 μM) | 0.1[a] |
| CHD solution (1.5 μM) | 0.75[b] |

[a]Assuming that metallic silver releases up to 0.2% of Ag$^+$.
[b]An upper limit concentration which corresponds to 25% higher amount than the quantity of CHD that was entrapped within the composite.

The vessels were kept in an incubated shaker at 26° C. under dark conditions. The disinfection kinetics were followed by sequentially sampling 1.0 ml aliquots form the vessels at the designated times. These samples were neutralized by dilution (1:1) with a neutralizing solution (0.2% w/w sodium thioglycolate, 1.9% w/w sodium thiosulphate, 1% w/w Tween 80, 1.4% w/w lecithin) for 5 min. The efficiency of this neutralization procedure was validated in separate control experiments. After neutralization, samples were serially diluted (10 fold) in phosphate buffer saline (PBS) and pour-plated with LB into Petri plates. The plates were incubated at 37° C. for 24 h and bacterial colonies were counted. The bactericidal experiments were repeated at least three times and the mean log reduction values (i.e. log $(N_t/N_0)$ where $N_t$=bacterial concentration at time t and $N_0$=bacterial concentration at time 0) for the various substances and thereof combinations were plotted vs. time.

Similar procedures were applied for the bactericidal effect of composites of the invention against *P. aeruginosa* PAO1 and PU21 and *S. epidermidis* ATCC 12228.

Material Characterization

Figure 1B:
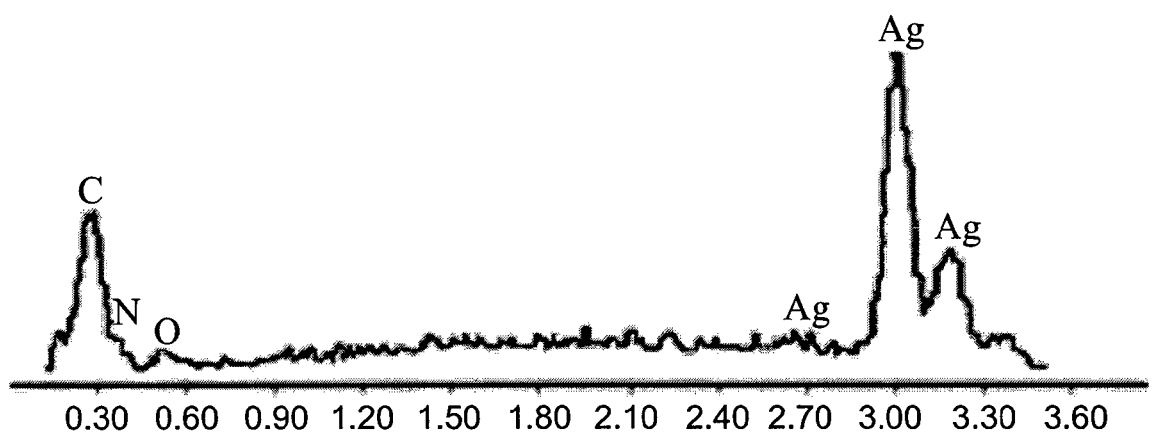

A typical HR-SEM image of the CHD@Ag composite is displayed in FIG. 1(a). It is seen that the composite powder is made of nanometric metallic crystallites which are aggregated into ~1 micron particles. Coupling EDAX analysis (FIG. 1(b)) with SEM imaging reveals the organic nature of the composite with the appearance of nitrogen, carbon and oxygen.

Figure 3:
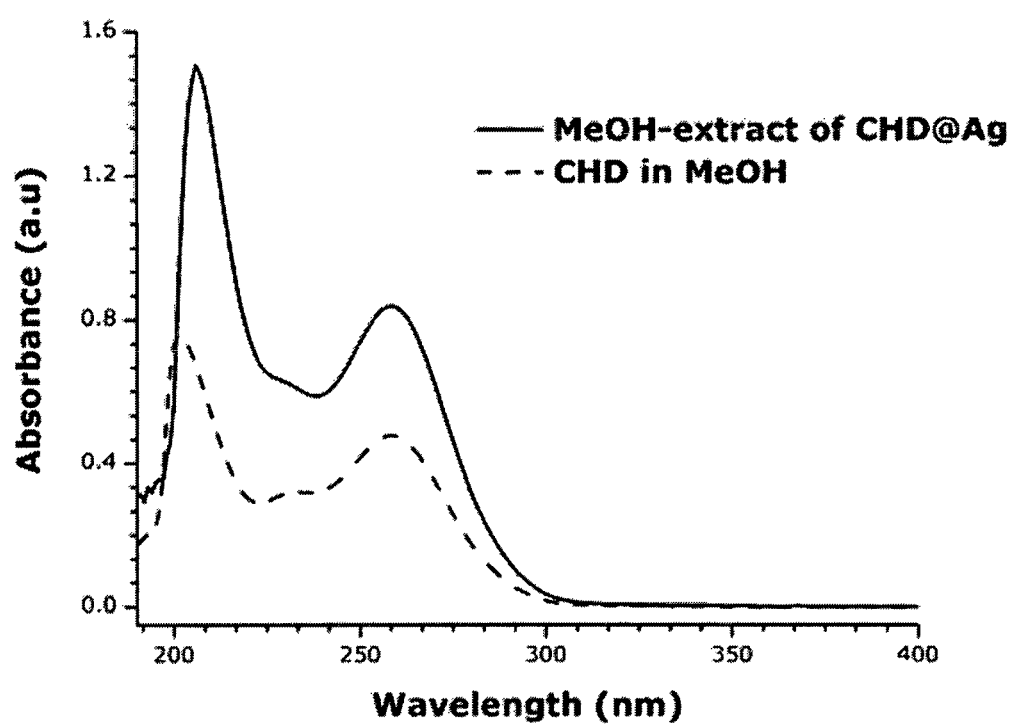
FIG. 3 shows the UV spectra of CHD in MeOH before entrapment and after extraction from CHD@Ag.

In order to examine the chemical stability of the CHD molecules towards the entrapment process, extraction experiment in MeOH was carried out. FIG. 3 compares the spectral analysis of the methanol-extract of CHD@Ag to that of CHD dissolved in MeOH, proving that the CHD molecules remain intact upon entrapment. The extraction experiment also provided the means to determine the amount of CHD present in the composite, which was found to be 0.19% mol CHD/mol silver.

Figure 2A:
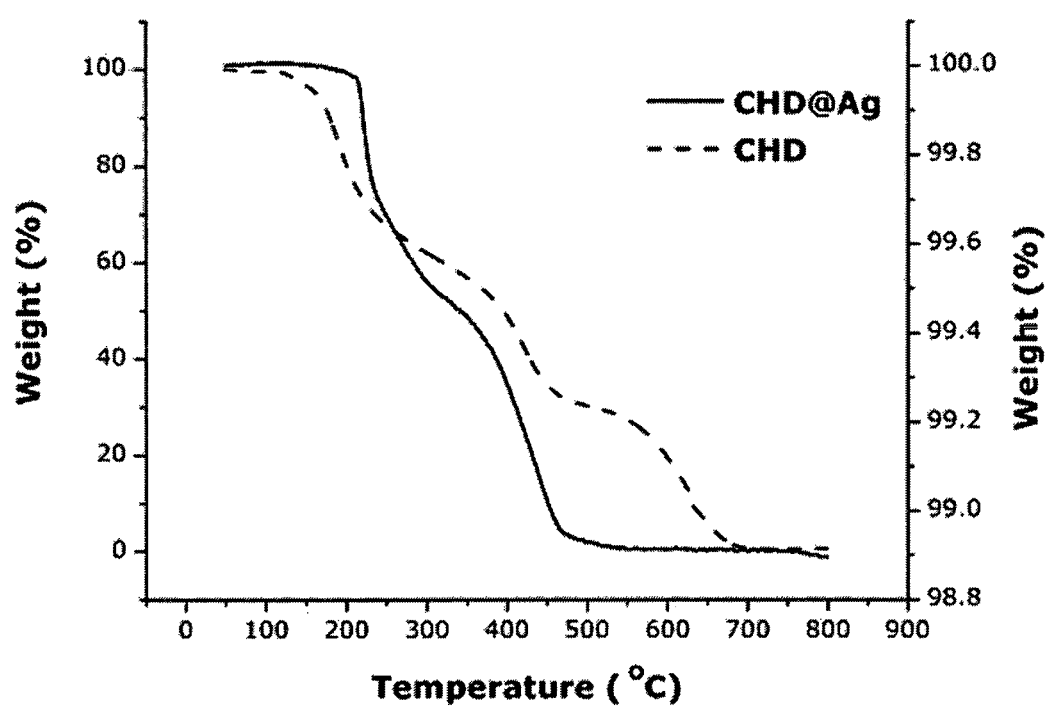
FIGS. 2A-2B shows a thermogravimetric analysis in air of pure CHD and CHD within CHD@Ag (FIG. 2A) and its first derivative (FIG. 2B).
Figure 2B:
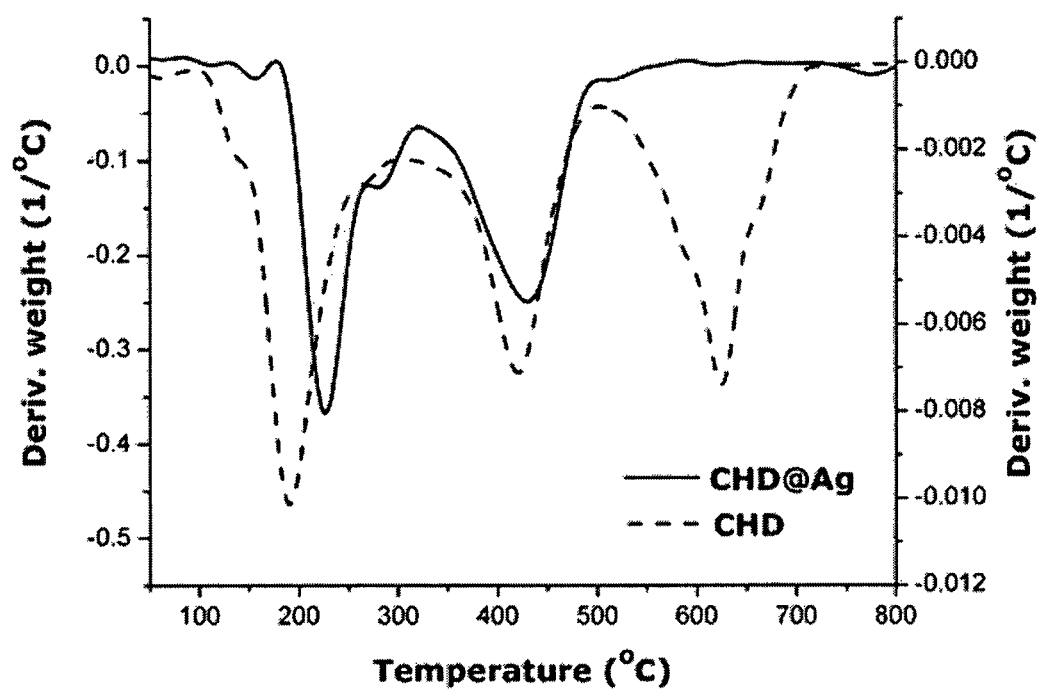

The thermogravimetric analysis (TGA) of CHD before and after entrapment within silver is shown in FIGS. 2A-2B. It is seen that the metal catalyzes the oxidative degradation of the entrapped CHD, narrowing the degradation temperature range from 100° C.-700° C. to 200° C.-500° C., eliminating the ~620° C. degradation step altogether, and shifting the two derivative peaks to lower temperatures. This catalytic effect of the metallic matrix on the oxidative degradation of the entrapped molecules has been observed previously in other studies of organic-metallic composites [1, 14], indicating the close proximity between the entrapped organic molecules and the metallic pore surface.

Figure 4:
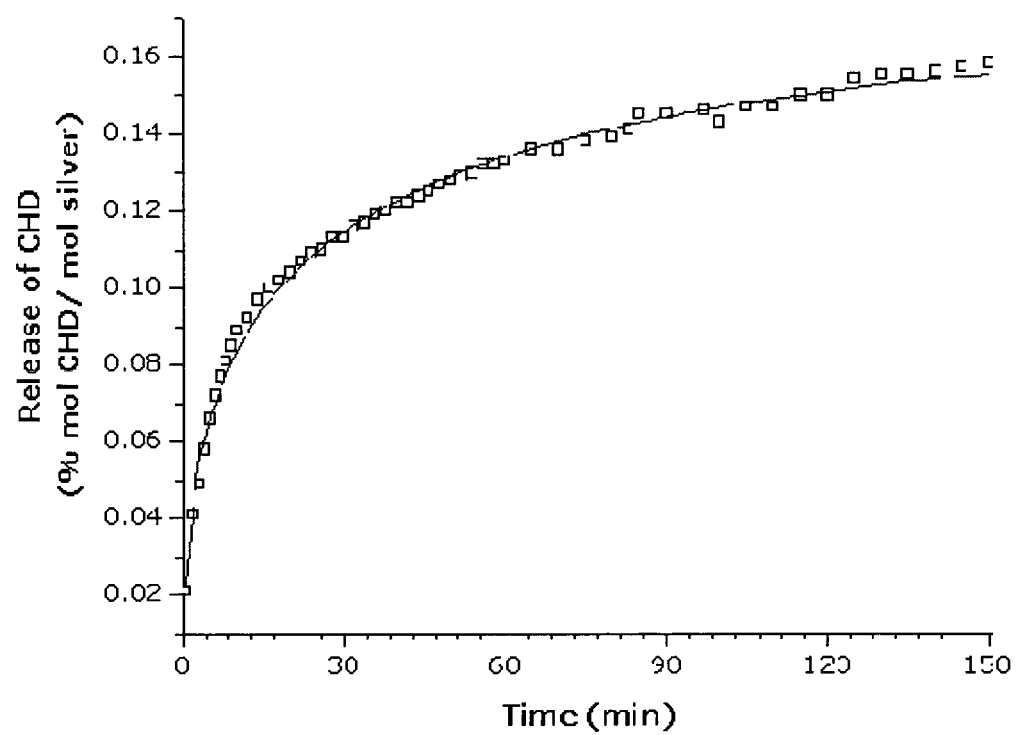
FIG. 4 shows the release profile of CHD from CHD@Ag and its fit to the Weibull model.

The kinetics of CHD leaching from the composite into HEPES buffer (which served as the bactericidal test medium) was tested and the results are presented in FIG. 4. It is seen that the release profile of the composite is characterized with a rapid release of about half the entrapped CHD molecules followed by a relatively slow release. This behavior was found to fit the Weibull model (Costa 2001):

$$m(t) = m_\infty \cdot \left[1 - \exp\left(-\left(\frac{t}{t_c}\right)^b\right)\right]$$

In the above formula, m(t) is the dopant fraction that is released into the extracting solvent at time t, $m_\infty$ is the total fraction which may be extracted by the chosen solvent (after infinite time), $t_c$ is a characteristic time, namely the time required for 63.2% (exp(−1)) of the total extractable population be extracted and b is a shape parameter, which i may have values between 0 and 1. If b=1, the model reduces to a simple 1$^{st}$-order model; if b<1, the curve is parabolic, with a higher initial slope (accommodating the initial "burst" observed in some extractions). The parameter b can thus be taken as an indication of the degree of homogeneity of the extractable population: a value near to 1 implies a relatively homogeneous extractable population with $t_c$ corresponding to its 1$^{st}$-order characteristic time, while a value far from 1 implies sample heterogeneity. For the curve in FIG. 4 the fitting parameters are $t_c$=26 min and b=0.45, with $m_{t=\infty}$=0.17%, $R^2$=0.99. This intermediate b value is thus indicative of the two CHD populations: The easily HEPES buffer-extractable accessible population and the slow released CHD. This heterogeneity of the release of CHD is also evident in the shape parameter, b=0.45, which points to the heterogeneity in the released populations. As will be shown later, this release profile dictates the kinetic biocidal profile of the composite. Finally, recalling that the total CHD population of the composite determined by the extraction experiment in MeOH is 0.19%, $m_{t=\infty}$=0.17% implies that about 10% of the entrapped population is held within the matrix much tighter.

Figure 5:
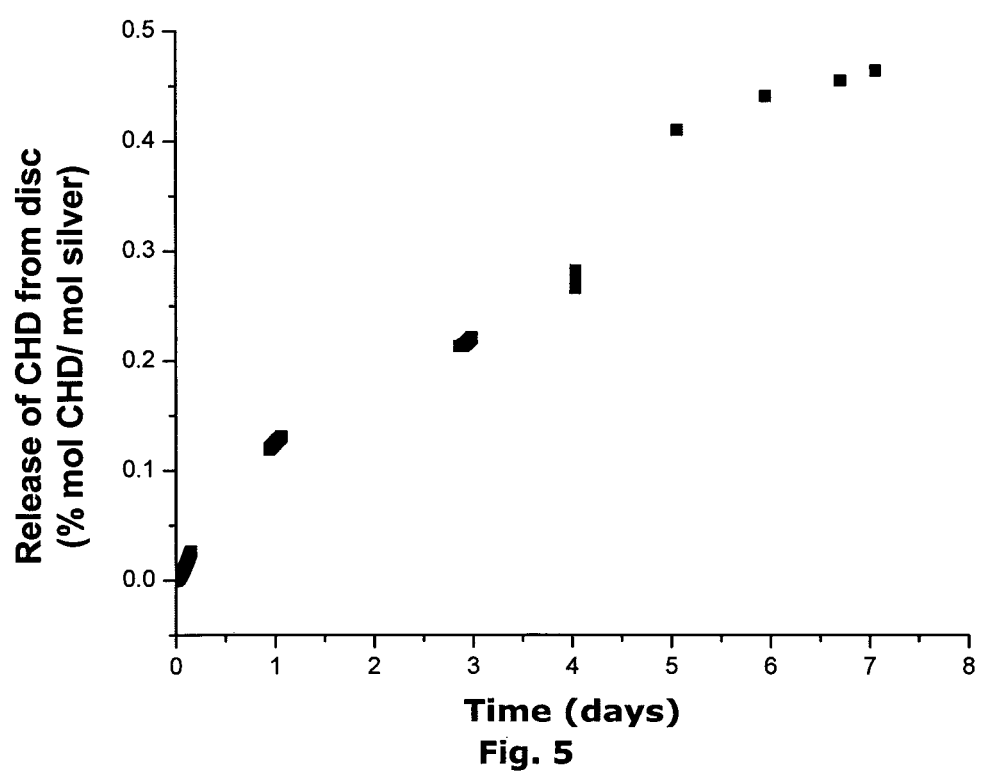
FIG. 5 shows the release of CHD from a disc of CHD@Ag

This rapid release kinetics of CHD can be controlled by pressing the composite powder into a disc. As it is seen in FIG. 5, the release of CHD from pressed composite disc into HEPES buffer solution is slowed down to an overall 7 days of continuous release. This decrease in the release kinetics is a result of the enclosure of pores and diffusion paths within the metallic matrix, which occurs when one applies pressure to the composite powder. This, in turn, limits the movement of the extracting solvent molecules within the composite and slows down its ability to extract the entrapped molecules.

It is important to note that adsorption of CHD on pre-made silver powder and entrapment of it within silver are completely different processes. Whereas adsorption takes place on the outer surface of the pre-aggregated metal and is a 2D-process, entrapment occurs during the aggregation of the metallic particles into a metallic powder, resulting in a 3D-configuration of host and dopant. Thus, while the entrapped molecules are confined within cages the walls of which are made of the metallic matrix with hindered access to the solvent, adsorbed molecules are freely facing the solution and thus can easily desorb. Even more striking is the observation that whereas CHD molecules do not tend to adsorb on the metal surface (below the detection limit), entrapment of CHD within the porous network of metallic aggregates occurs as described above. This, in turn means that the entrapment is mainly physical engaging of CHD molecules within the interstitial porosity and cages of the metallic porous network, which allows their release when needed.

The Biocidal Activity of a CHD@Ag Composite

Figure 6:
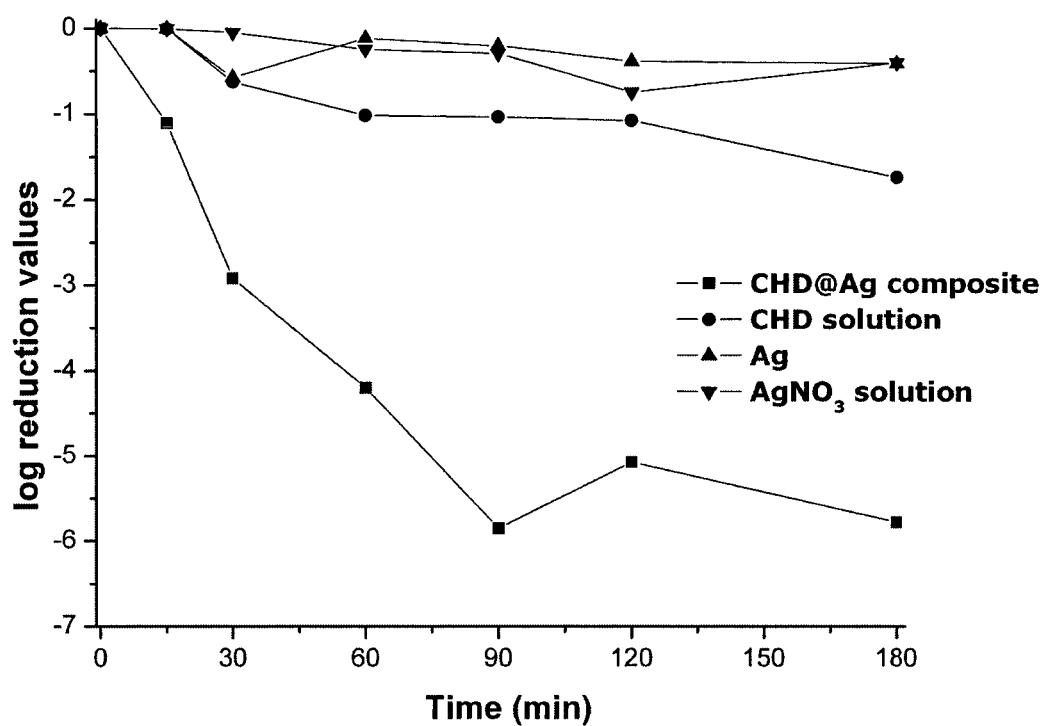
FIG. 6 shows the kinetic profile of the bactericidal activity of CHD@Ag composite compared to CHD solution, and to silver towards $E.\ coli$ MG1655.

FIG. 6 shows the striking synergetic effect of CHD@Ag powder towards *E. coli* MG1655. It is seen that this strain is only slightly affected by exposure to silver at the tested concentration; that CHD solution exhibits only very weak biocidal activity; and that $Ag^+$ (from $AgNO_3$) to which a role has been attributed in the activity of Ag, shows no biocidal activity at the given concentration. In contrast, CHD@Ag exhibits highly efficient biocidal activity reducing the population of bacteria to practically zero (note the logarithmic scale) after 90 min. In order to make the comparison with metallic silver relevant, the metallic silver matrix that was used was derived from a CHD@Ag composite from which all of the CHD was extracted.

Figure 7:
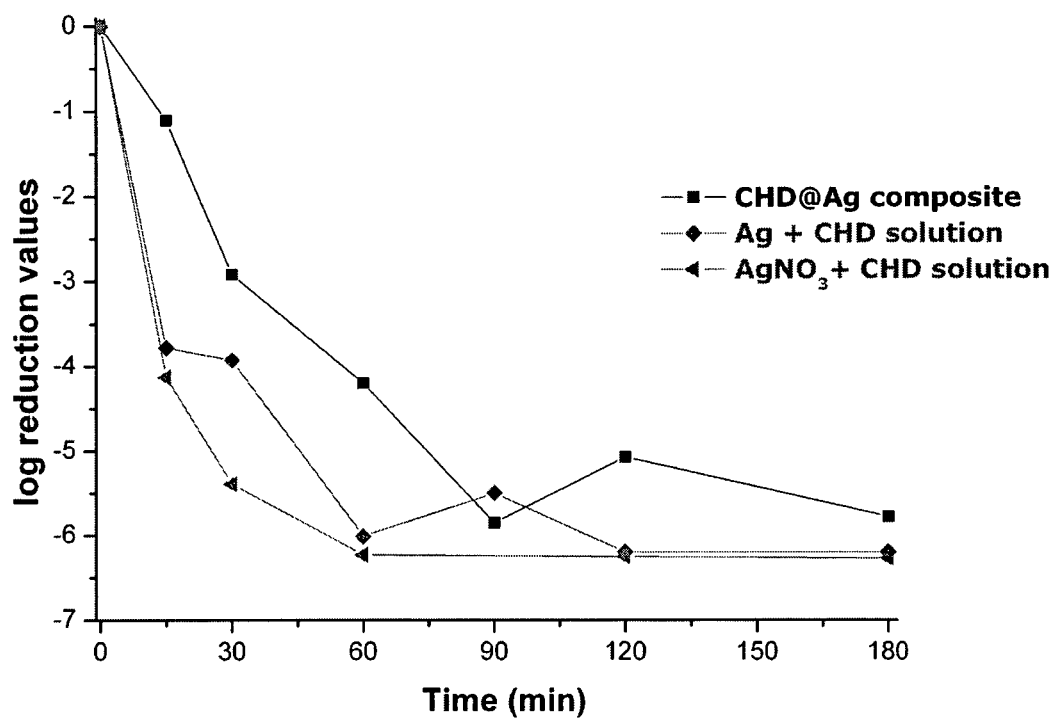
FIG. 7 shows the kinetic profile of the bactericidal activity of CHD@Ag composite compared to CHD-Ag mix combinations towards $E.\ coli$ MG1655.

FIG. 7 shows the kinetic profile of the bactericidal activity of CHD@Ag composite compared to CHD-Ag mixtures towards *E. coli* MG1655. As can be seem from FIG. 7 the advantage of CHD@Ag is demonstrated by its longer action, compared to the fast action of the two combinations.

The efficacy of CHD@Ag composite of the invention was tested against gram positive and gram negative prototypes bacteria which are associated with skin infections, namely *Pseudomonas aeruginosa* and *Staphylococcus epidermidis*.

Figure 8:
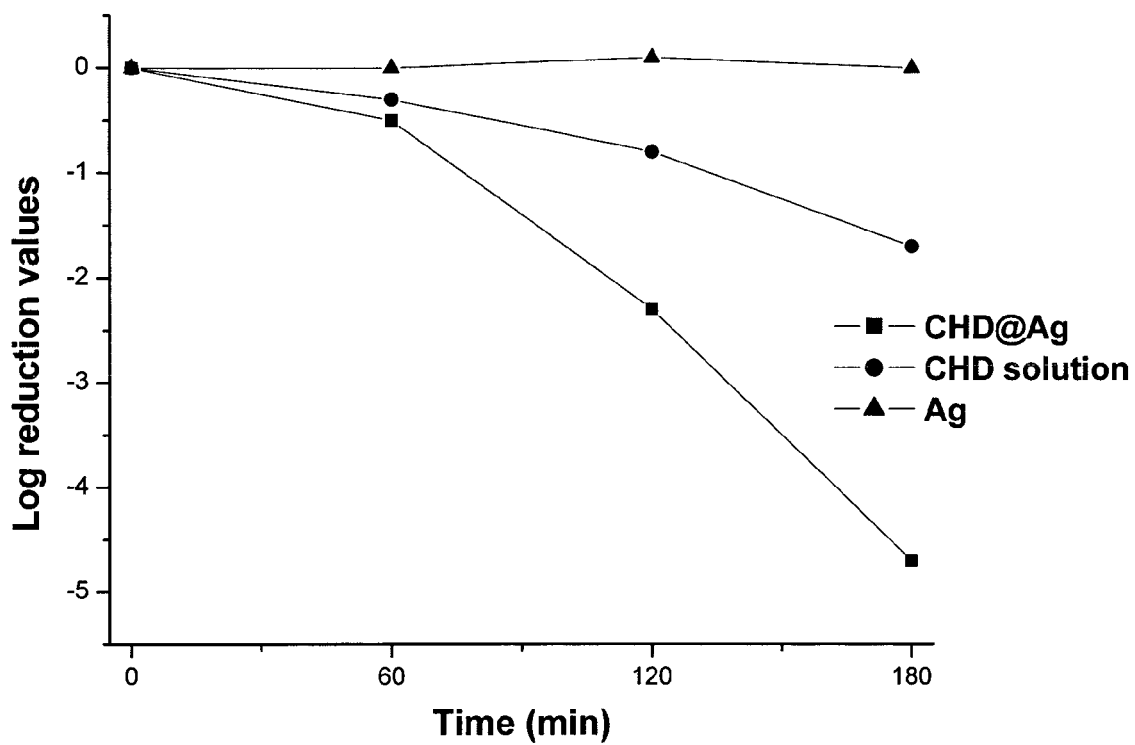
FIG. 8 shows the kinetic profile of the bactericidal activity of CHD@Ag composite towards $P.\ aeruginosa$ PU21.

FIG. 8 shows the bactericidal activity profile of CHD@Ag composite powder towards *P. aeruginosa* PU21 compared to that of CHD solution and of silver. As it is seen for *E. coli* above, the CHD@Ag composite exhibits a synergistic bactericidal effect of its ingredients: Whereas silver has practically no effect on *P. aeruginosa* PU21 population and solution of CHD shows a weak bactericidal effect, the CHD@Ag composite exhibits a strong bactericidal action, reducing the bacterial population to zero within 3 hours.

Figure 9:
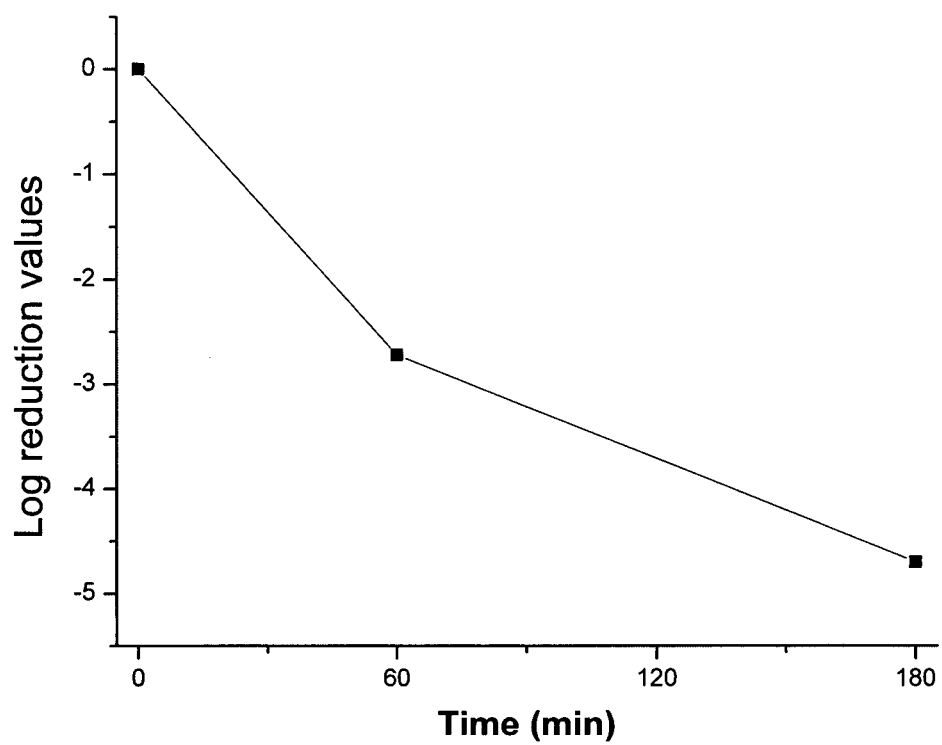
FIG. 9 shows the kinetic profile of the bactericidal activity of CHD@Ag composite towards $P.\ aeruginosa$ PAO1.
Figure 10:
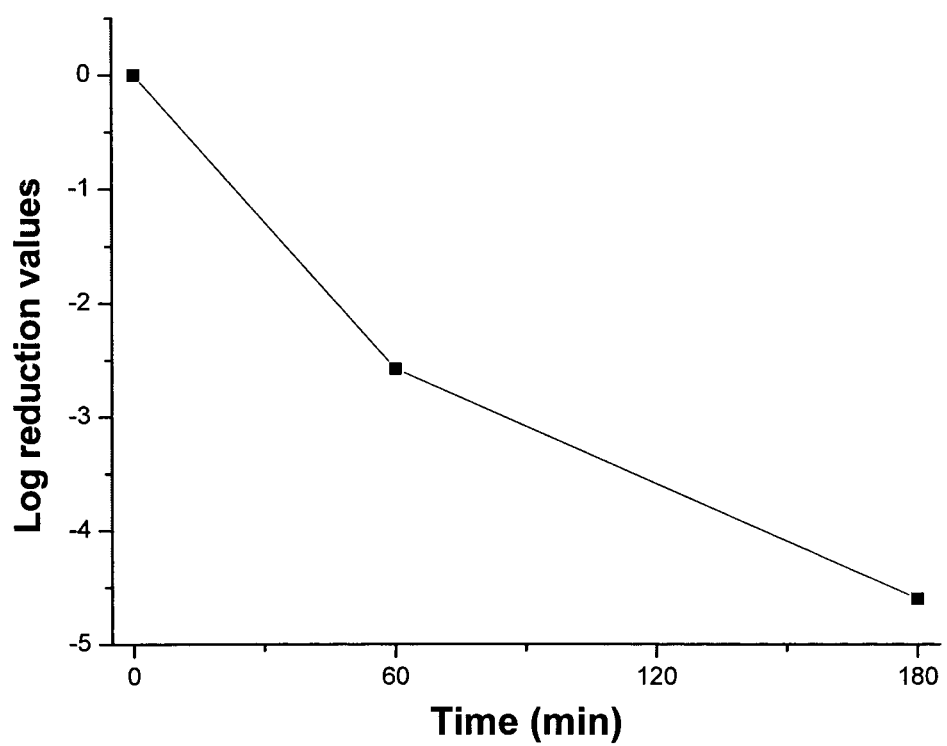
FIG. 10 shows the kinetic profile of the bactericidal activity of CHD@Ag composite compared to towards $S.\ epidermidis$ ATCC 12228.

FIGS. 9 and 10 show the bactericidal action of CHD@Ag towards *P. aeruginosa* PAO1 and *S. epidermidis* ATCC 12228. Here too, it is evident that exposing these two gram-negative and gram-positive bacteria to the CHD@Ag composite powder eliminates efficiently their bacterial populations within 3 hours.

Entrapment within Copper Matrix

Copper is another metal which exhibits biocidal activity towards a broad range of bacteria, fungi and viruses. Compared to silver, copper is much cheaper and hence the interest in its use as an alternative biocidal metal. Composites and products comprising biocidal copper may be impregnated in fabrics, particularly in fabrics destined for the production of items worn on body parts which exert sweat (such as foot ulceration treatment), water purification and more.

CHD@Cu was prepared by similar procedures to that of CHD@Ag except that a higher temperature was applied in order for increase the reducing power of sodium hypophosphite.

Figure 11:
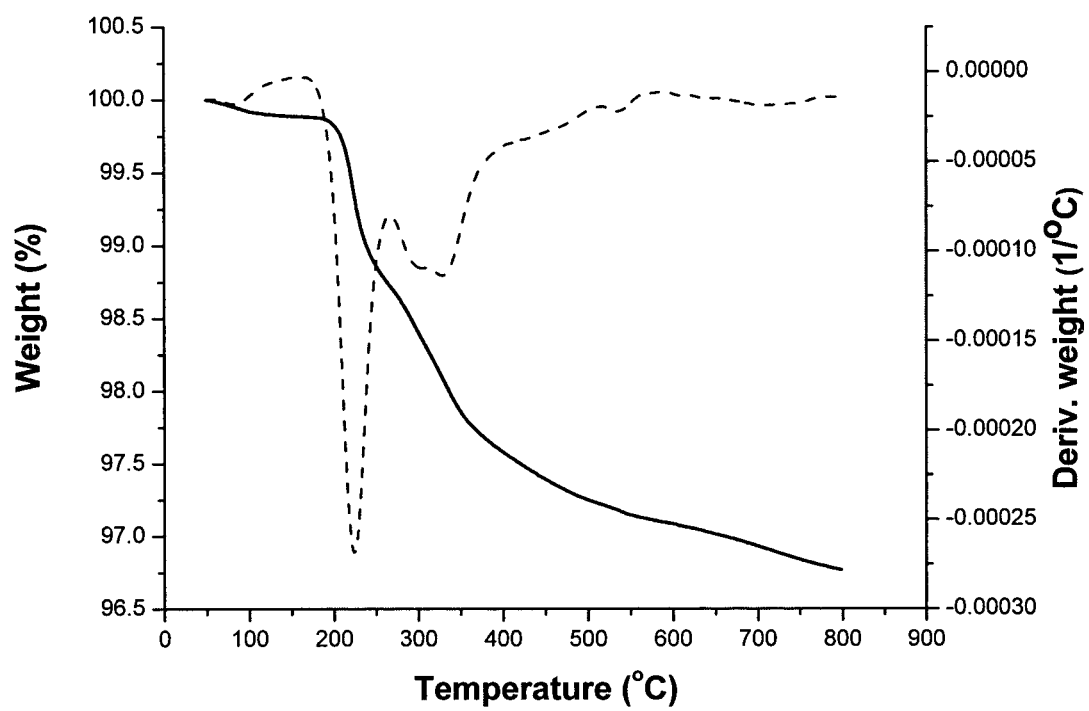
FIG. 11 shows a thermogravimetric analysis of CHD@Cu composite under nitrogen (solid curve) and its first derivative (dotted curve).

FIG. 11 presents the thermogravimetry analysis of CHD@Cu under nitrogen (as copper is oxidized under air). It is seen that under these conditions, the CHD@Cu composite looses about 3% of its weight due to carbonization of the entrapped CHD molecules and thus revealing the presence of organic moieties within the composite.

Figure 12:
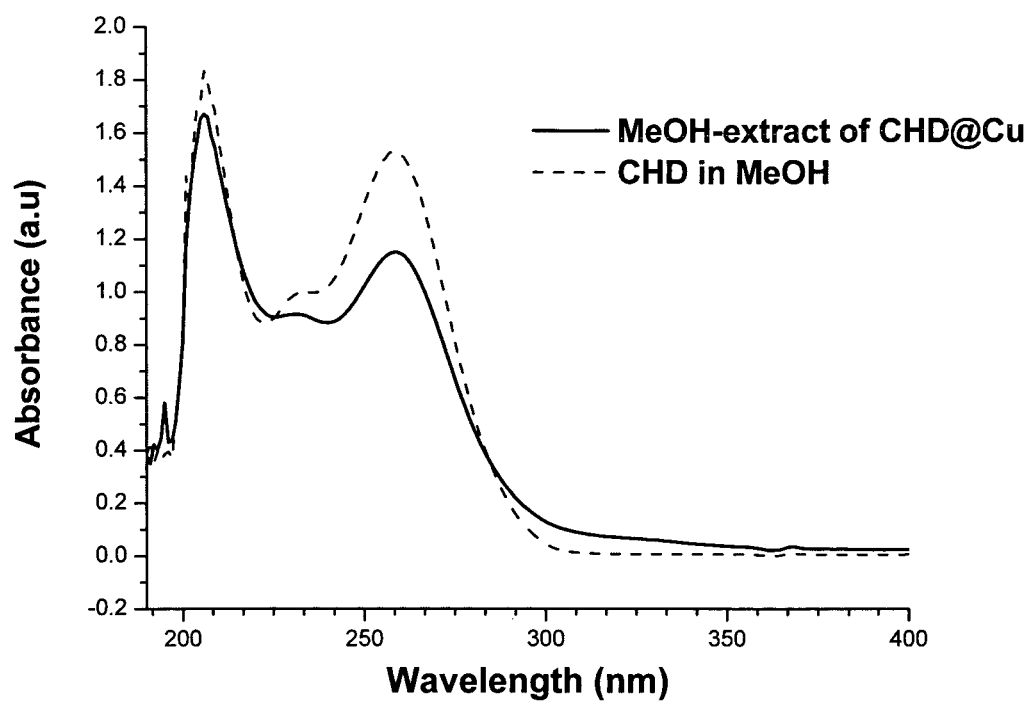
FIG. 12 shows UV spectra of CHD in MeOH before entrapment and after extraction from CHD@Cu composite.

The stability of CHD molecules towards their entrapment within copper is shown in FIG. 12. Comparing the absorbance spectrum of MeOH-extract to that of CHD dissolved in MeOH, shows that the CHD molecules are not influenced by the entrapment process. As mentioned above, the extraction with MeOH also indicates the quantity of the CHD present in the composite, which was found to be 0.16% mol CHD/mol copper.

Figure 13A:
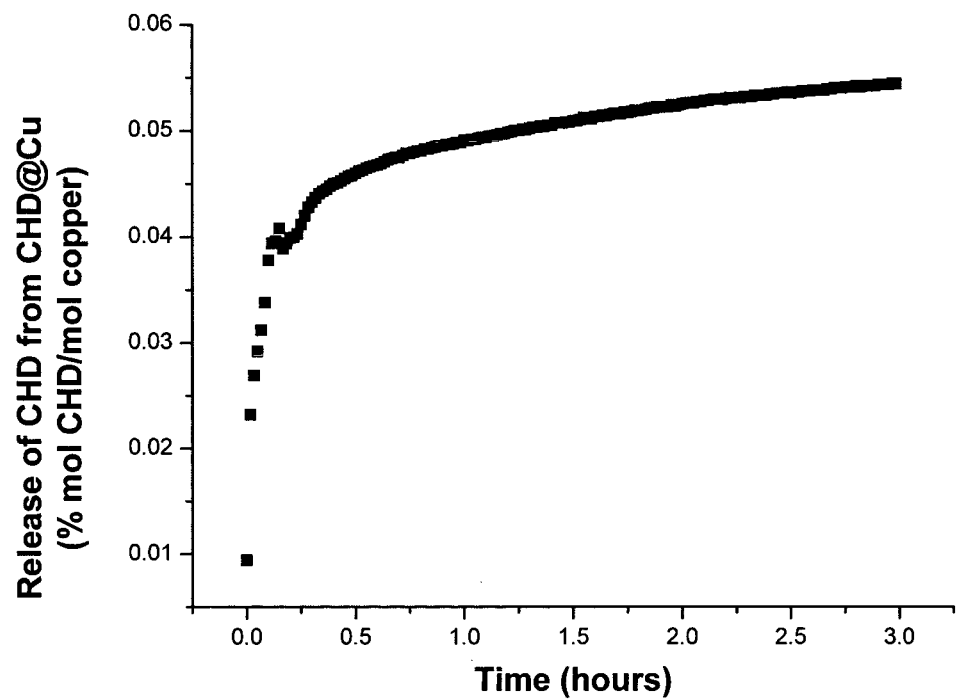
FIGS. 13A-13B shows the release profile of CHD from CHD@Cu composite in short terms (FIG. 13A) and in longer terms (FIG. 13B).
Figure 13B:
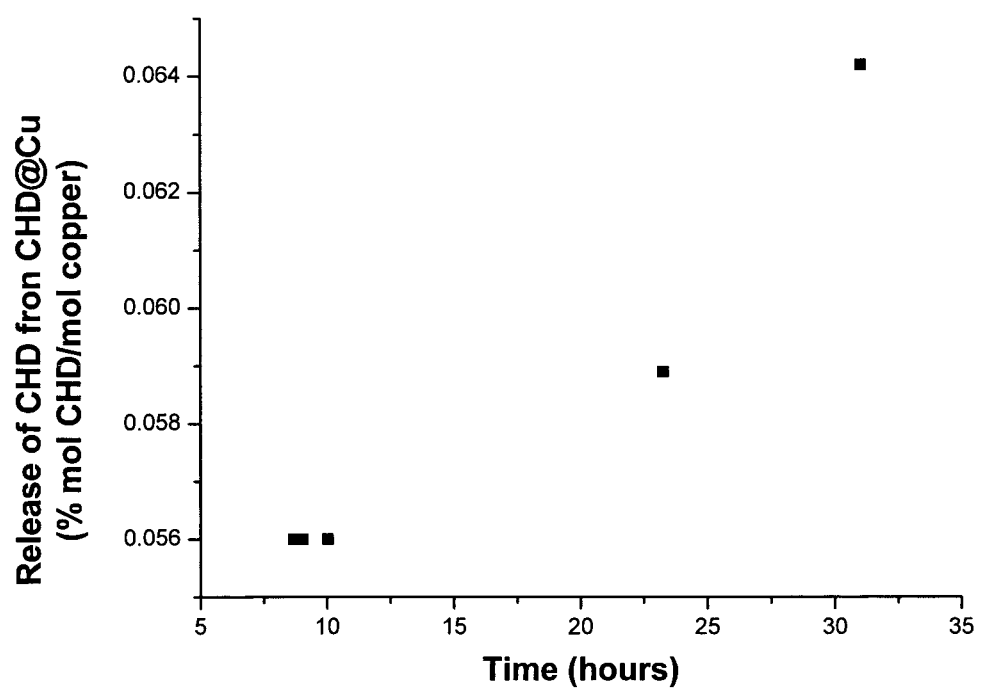

The release profile of CHD from CHD@Cu into HEPES, which was used as a medium for the bactericidal tests, is shown in FIG. 13. Bearing in mind that the total entrapped population is 0.16% mol CHD/mol copper, it is seen that the release profile follows bi-modal release kinetics: rapid release of ~30% of the entrapped CHD followed by slow and constant release of the rest of the entrapped population.

The invention claimed is:

1. A composite consisting of a metallic matrix formed by at least one metal, or an alloy thereof, entrapping within it at least one bioactive agent, wherein said metal matrix has an average pore size of between about 0.1 to about 30 nm and wherein said composite controllably releases at least one of said bioactive agent and metal or ion thereof.

2. A composite consisting of a metallic matrix formed by at least one metal, or an alloy thereof, entrapping within it at least one therapeutically active agent, wherein said metal matrix has an average pore size of between about 0.1 to about 30 nm and wherein said composite controllably releases at least one of said therapeutically active agent and metal or ion thereof.

3. A composite consisting of a metallic matrix formed by at least one metal, or an alloy thereof, entrapping within it at least one biocidal agent, wherein said metal matrix has an average pore size of between about 0.1 to about 30 nm and wherein said composite controllably releases at least one of said biocidal agent and metal or ion thereof.

4. A composite according to claim 1, wherein at least one metal is selected from Au, Ag, Cu, Zn, Pt, Pd, Ti and Co, or any combination thereof.

5. A composite according to claim 1, wherein said at least one bioactive agent is selected from anti-bacterial agent, anti-viral agent, anti-fungal agent, anti-inflammatory agent, biocidal agent, antiseptic agent, antibiotic, endocrinic agent, anti-proliferative agent, anti-depressant, psychiatric agent, anaesthetic agent or any combinations thereof.

6. A composite according to claim 2, wherein said at least one therapeutically active agent is a topically administered agent.

7. A composite according to claim 2, wherein said at least one therapeutically active agent is used in the treatment of a topical condition, disease or disorder.

8. A composite according to claim 2, wherein said at least one therapeutically active agent is at least one biocidal agent.

9. A composite according to claim 1, wherein the weight ratio between said at least one entrapped agent and at least one metal is from about 0.05 to about 20.

10. A composite consisting of a metallic matrix formed by at least one metal, or an alloy thereof, entrapping within it at least one bioactive agent, wherein said composite controllably releases at least one of said bioactive agent and metal or ion thereof and wherein said controlled release of said at least one agent is in a rate of about half-content said at least one agent per hour to about half-content said at least one agent per month.

11. A method of disinfecting water comprising contacting water with an effective amount of at least one composite according to claim 3.

* * * * *